United States Patent [19]

Cahn et al.

[11] 4,058,575
[45] Nov. 15, 1977

[54] CATALYST PRETREATMENT WITH HYDROCARBON FEEDSTOCK

[75] Inventors: Robert P. Cahn, Millburn; John P. Longwell, Westfield, both of N.J.

[73] Assignee: Exxon Research & Engineering Co., Linden, N.J.

[21] Appl. No.: 586,177

[22] Filed: June 12, 1975

[51] Int. Cl.² .......... C07C 13/00; C07C 3/56; C07C 5/28; B01J 27/38
[52] U.S. Cl. .......... 260/666 P; 208/108; 252/414; 260/671 R; 260/683.47; 260/683.68
[58] Field of Search .......... 252/414, 415; 260/674 R, 666 P, 683.68, 671 R

[56] References Cited

U.S. PATENT DOCUMENTS

| | | | |
|---|---|---|---|
| 2,683,763 | 7/1954 | Lien et al. | 208/280 |
| 2,683,764 | 7/1954 | Lien et al. | 208/280 |
| 3,809,728 | 5/1974 | Kemp | 252/415 |
| 3,830,871 | 8/1974 | Mayer et al. | 260/683.74 |
| 3,851,004 | 11/1974 | Yang | 260/671 C |
| 3,852,184 | 12/1974 | Siskin et al. | 260/666 P |
| 3,873,635 | 3/1975 | Prescott et al. | 260/683.57 |
| 3,880,945 | 4/1975 | Kramer | 260/683.68 |
| 3,907,913 | 9/1975 | Kemp | 260/683.68 |

FOREIGN PATENT DOCUMENTS

| | | | |
|---|---|---|---|
| 291,406 | 3/1971 | U.S.S.R. | 252/414 |

Primary Examiner—Winston A. Douglas
Assistant Examiner—P. E. Konopka
Attorney, Agent, or Firm—John W. Ditsler

[57] ABSTRACT

Partially deactivated hydrocarbon conversion catalysts comprising (a) one or more Lewis acids of the formula $MX_n$ where M is a metal selected from Group III-A, IV-B, V or VI-B elements of the Periodic Table, X is a halogen, $n$ is the ratio of halogen atoms to atoms of M and varies from 1-8, and (b) a strong Bronsted acid are contacted with a hydrocarbon feedstock to recover the active or potentially active catalyst species from the partially deactivated catalyst stream prior to regeneration. In addition, potential organic and inorganic catalyst poisons present in said feedstock are removed therefrom during said contacting prior to introducing said feedstock into a hydrocarbon conversion process.

13 Claims, 2 Drawing Figures

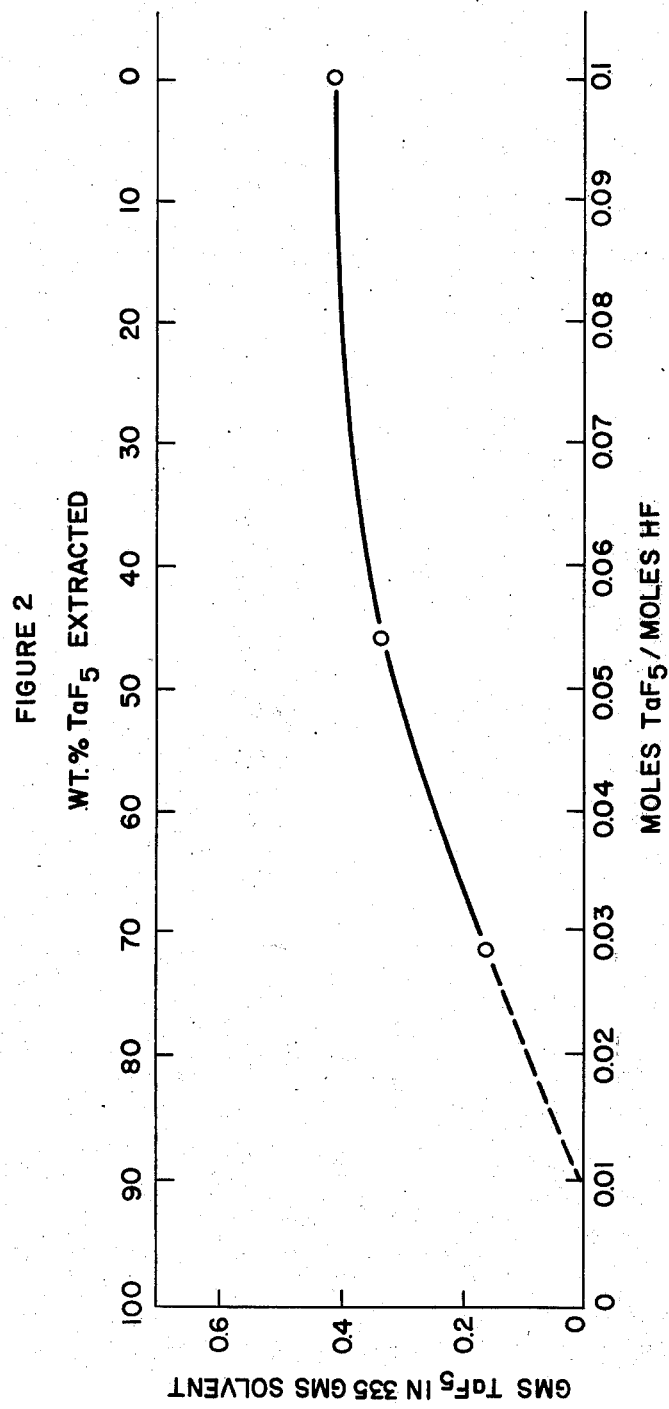

CATALYST PRETREATMENT WITH HYDROCARBON FEEDSTOCK

BACKGROUND OF THE INVENTION

1. Field of the Invention

The present invention relates to a process for recovering the active or potentially active species from a partially deactivated hydrocarbon conversion catalyst. More particularly this invention relates to a process for extracting with a hydrocarbon feedstock the active or potentially active species from a partially deactivated catalyst comprising (a) one or more Lewis acids of the formula $MX_n$ where M is selected from Group III-A, IV-B, V or VI-B elements of the Periodic Table, X is a halogen, $n$ is the ratio of halogen atoms to atoms of M and varies from 1-8, and (b) a strong Bronsted acid. The preferred Lewis and Bronsted acids are tantalum or niobium pentafluoride or mixtures thereof and hydrogen fluoride, respectively.

DESCRIPTION OF THE PRIOR ART

Hydrocarbon conversion processes involving the use of metal halide based catalysts have been extensively described in the prior art. For example, U.S. Pat. Nos. 2,683,763 and 2,683,764 disclose that tantalum pentafluoride or columbium pentafluoride in combination with hydrogen fluoride can be used for the refining of hydrocarbon oils or to promote the disproportionation of alkyl-substituted aromatic materials. The patentees also disclose that hydrogen fluoride/tantalum pentafluoride and hydrogen fluoride/columbium pentafluoride are powerful catalysts for isomerization, alkylation, cracking and other reactions of aromatics. U.S. Patent 3,708,553 teaches that high octane alkylates can be produced by contacting paraffinic and/or alkyl substituted aromatic hydrocarbons with olefins in the presence of a catalyst comprising one or more metal halides and a strong Bronsted acid selected from the group consisting of fluorosulfuric acid and trifluoromethanesulfonic acid and mixtures thereof. In addition, Venezuelan Pat. No. 31,267 teaches the isomerization of saturated acyclic and alicyclic hydrocarbon materials in the presence of a catalyst combination comprising a difficultly reducible metal halide, preferably a metal fluoride, in combination with at least a molar equivalent of hydrogen halide.

As the reactions in such hydrocarbon conversion processes proceed, potential catalyst poisons such as oxygen, sulfur, nitrogen, and metallic compounds present in the hydrocarbon feedstock may accumulate within the catalyst system such that the catalyst gradually becomes partially spent or deactivated to such a degree that it is no longer suited for continued use in said processes. Since it is often difficult if not impossible to selectively separate the portion remaining active from the portion which has become deactivated, the catalyst regeneration system must be sized to handle both active and deactivated material. It has been suggested in U.S. Pat. No. 2,394,929 to reactivate a partially deactivated catalyst using the saturated portion of the hydrocarbon alkylation feedstock so as to extract catalyst poisons and thereby improve catalyst activity to decrease the load on the regeneration step. However, nowhere in the prior art is there taught a one-step method for extracting the active or potentially active species from a partially deactivated hydrocarbon conversion catalyst using a hydrocarbon feedstock while simultaneously removing substantially all of the potential catalyst poisons present in said feedstock prior to introducing said feedstock into a hydrocarbon conversion process.

SUMMARY OF THE INVENTION

In accordance with the present invention, it has now been discovered that the active or potentially active catalyst species from at least a portion of a partially deactivated hydrocarbon conversion catalyst comprising (a) one or more Lewis acids of the formula $MX_n$ where M is a component selected from Group III-A, IV-B, V or VI-B elements of the Periodic Table of their mixtures, X is a halogen, $n$ is the ratio of halogen atoms to atoms of M and varies from 1 to 8, and (b) a strong Bronsted acid may be extracted therefrom by contact with a refined or an unrefined hydrocarbon feedstock, i.e. one that has not been treated for the removal of potential catalyst poisons, the potential catalyst poisons present in said feedstock being substantially removed therefrom during said extraction. The extraction process of the present invention is conducted substantially in the liquid phase. Temperatures and pressures are not critical to the practice of the present invention and may range broadly. Preferably, the extraction is carried out in the presence of hydrogen.

The present process is based on the premise that the active or potentially active catalyst components are more hydrocarbon soluble while the inactive catalyst species are essentially hydrocarbon insoluble. Thus, contacting the partially deactivated catalyst with the hydrocarbon feedstock results in active or potentially active catalyst components being preferentially dissolved or solubilized in the feedstock and the inactive or deactivated catalyst species being rejected. Additionally, it is believed that the inactive catalyst species are primarily associated with the Lewis acid component of the catalyst, said acid having an affinity for the potential catalyst poisons present in the hydrocarbon feedstock. Therefore, the poisons will be extracted from said feedstock via the acid. Further, any catalyst poisons present in the feedstock will convert at least a portion of the active or potentially active catalyst still present in the partially deactivated catalyst stream being treated into inactive species. Since the present extraction process separates active from inactive catalyst species, the amount of catalyst poisons that would otherwise be introduced into the hydrocarbon conversion process is also reduced. Thus there results from the process of the present invention an extract phase comprising the active or potentially active catalyst species and the hydrocarbon feedstock which is substantially free of contaminants and a raffinate phase comprising deactivated catalyst species and substantially all of said contaminants. In a preferred embodiment of this invention, at least a portion of the extract phase is introduced into the hydrocarbon conversion process.

BRIEF DESCRIPTION OF THE DRAWINGS

FIG. 2 is a graph summarizing extraction studies for the tantalum pentafluoride/hydrogen fluoride catalyst system.

DETAILED DESCRIPTION OF THE INVENTION

Figure 1:
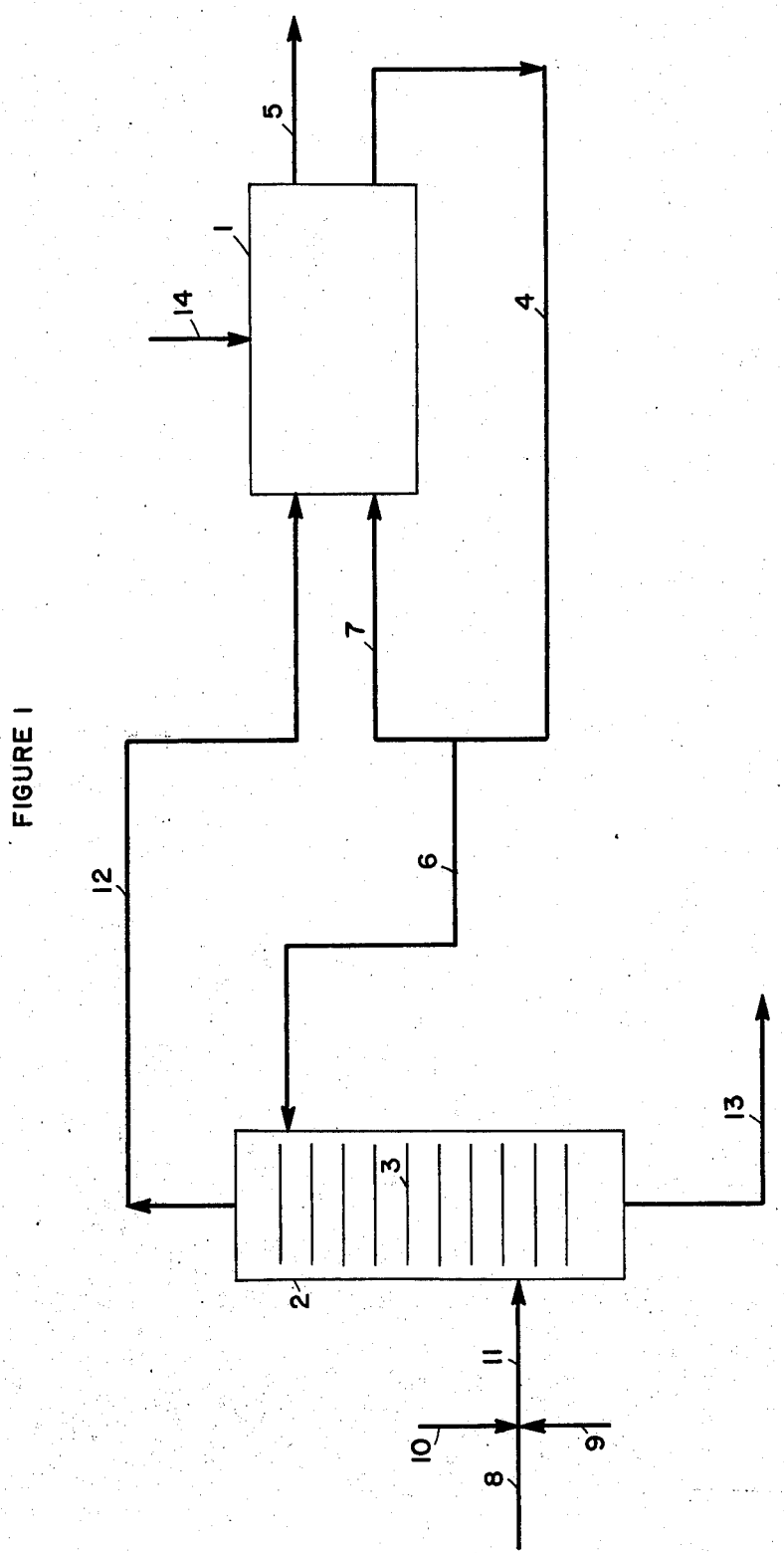
FIG. 1 is a flow diagram of one embodiment of the present invention.

In a typical hydrocarbon conversion process, the catalyst becomes gradually deactivated by poisons that are introduced into the reaction zone with the feed, by contaminants formed in the reaction zone, and by catalyst decomposition and degradation processes occurring within the reaction zone. In order to maintain catalyst activity at a satisfactory level in a continuous process, it is necessary to periodically or continuously withdraw or purge at least a portion of the partially deactivated catalyst from the system, and make-up the catalyst inventory with fresh or regenerated make-up catalyst. It is this continuously withdrawn "purge" catalyst which is being treated by the process of the present invention.

The catalyst purge stream must contain some active catalyst since said stream was withdrawn from a pool of catalyst actively engaged in hydrocarbon conversion. It is, therefore, a great advantage is a separation between active and deactivated catalyst present in the purge stream can be achieved, and if the active catalyst thus separated from the inactive portion can be recycled to the conversion process, while only the inactive portion is further processed, i.e. regenerated. The present invention achieves precisely this goal while at the same time pretreating the hydrocarbon conversion process feed with material already scheduled for regeneration.

The present invention is particularly suited for use with a hydrocarbon conversion catalyst which comprises (a) one or more Lewis acids of the formula $MX_n$ where M is a component selected from the Group III-A, IV-B, V or VI-B elements of the Periodic Table or their mixtures, X is a halogen, preferably fluorine, $n$ is the ratio of halogen atoms to atoms of M and varies from 1–8, and (b) a strong Bronsted acid, preferably a hydrogen halide. The Periodic Table referred to is that described in "The Encyclopedia of Chemistry", Reinhold Publishing Corporation, 2nd Ed. (1966) at page 790. The term "elements" as used herein refers to the metals and metalloids of the aforementioned Groups of the Periodic Table.

The above-mentioned catalyst system is composed of one or more Lewis acids and a Bronsted acid. Metal halids are the preferred Lewis acids. Useful halides constituents include the fluorides, bromides and chlorides of titanium, vanadium, zirconium, niobium, phosphorus, tantalum, chromium, molybdenum, tungsten, arsenic, antimony, bismuth and the chlorides and bromides of gallium and aluminum. Group IV-B, V and VI-B metal fluorides are preferred metal halides, Group V being most preferred. Specific examples of useful metal fluorides include antimony pentafluoride, tantalum pentafluoride, niobium pentafluoride, vanadium pentafluoride, tungsten hexafluoride, titanium tetrafluoride, molybdenum hexafluoride, bismuth pentafluoride, arsenic pentafluoride, mixtures thereof and the like. The most preferred metal halide catalyst constituents are tantalum and niobium halides, preferably tantalum pentafluoride, niobium pentafluoride and mixtures thereof.

The second component of the catalyst system is a Bronsted acid. Suitable Bronsted acids include a hydrogen halide, halogenated and unhalogenated sulfuric acids, acetic acids, phosphoric acids, sulfonic acids and the like. The Bronsted acid may also be admixed with a portion of its corresponding anhydride. The preferred Bronsted acid is a hydrogen halide, fluorosulfonic acid, trifluoromethanesulfonic acid, methane sulfonic acid, trifluoroacetic acid, sulfuric acid and the like. Useful hydrogen halides include hydrogen bromide, hydrogen chloride, and hydrogen fluoride. The preferred hydrogen halide catalyst constituent is hydrogen fluoride.

The effectiveness of the catalyst described above when used in a hydrocarbon conversion process is related to the molar ratio of Bronsted acid to Lewis acid. While relatively minor amounts, i.e. less than equimolar amounts, of Bronsted acid relative to Lewis acid, will dissolve at least a portion of the Lewis acid and thereby effect the reaction, the rate of reaction will inordinately slow. However, the reaction rate, i.e. the yield in a given period of time, will be increased if at least an equimolar amount of Bronsted acid relative to Lewis acid is present in the reaction zone. Increasing the mole ratio of Bronsted acid to Lewis acid above one provides additional Bronsted acid so as to dissolve more of the Lewis acid and thereby provide an increasing amount of liquid phase catalyst which will favor an increased reaction rate. The effect of increasing amounts of liquid phase catalyst on reaction rate becomes more pronounced as the mole ratio of Bronsted acid to Lewis acid exceeds one and continues as the liquid phase of the catalyst increases. Thus, the mole ratio of Bronsted acid (hydrogen halide) to Lewis acid (metal halide) is preferably at least 2:1 and more preferably at least 5:1. The favorable effects mentioned above will ultimately level off as the Bronsted acid dilutes the acidity of the reaction system. Depending upon the relative amounts of catalyst constituents used, the catalyst may be a homogeneous solution of the Lewis acid and the Bronsted acid or a mixture of solid and dissolved Lewis acid in Bronsted acid.

As used herein, the term "potentially active catalyst species" refers to the Lewis acid component of the catalyst. The term "active catalyst species" refers to the Lewis acid component of the catalyst when contacted with a sufficient amount of Bronsted acid or a substance that will generate a protonic acid upon contact with the Lewis acid so that the catalyst so formed can be employed effectively in a hydrocarbon conversion process as described above. As an example, tantalum pentafluoride is a potentially active catalyst species which becomes active when contacted with at least an equal molar amount of hydrogen fluoride.

The catalyst may be used as the neat liquid or as a diluted solution. Any diluent or solvent may be used that is inert to the catalyst under the particular hydrocarbon conversion reaction conditions. Typical diluents or solvents include sulfuryl chloridefluoride, sulfuryl fluoride, sulfolane, fluorinated hydrocarbons, polyfluorinated-polyhalogenated hydrocarbons, Freons, acid anhydrides, mixtures thereof and the like. When a solvent or diluent is used, sufficient amounts are employed to maintain the viscosity of the reaction mixture at a desired level. The amount of diluent employed can vary appreciably and can range as high as 98 volume % of the reaction mixture. Preferably, the ratio of diluent to catalyst volume will range from about 20:1 to 1:1. Higher dilutions may be desirable, for example, in those reactions that proceed with high exothermicity.

In general, the partially deactivated catalyst may be derived from those reaction and side reactions that occur under the influence of Friedel-Craft's catalysts, e.g., isomerization, alkylation, polymerization, hydrocracking and the like. The present invention is particularly applicable to isomerization and alkylation reactions. Typical isomerizable feedstocks include acyclic and alicyclic aliphatic hydrocarbons having at least four carbon atoms that are converted to a product enriched in an isomer thereof. Typically, acyclic hydrocarbons having at least four carbon atoms, that is straight chain or branched chain paraffins having from about 4 to 10 carbon atoms, preferably from about 4 to 8 carbon atoms, are converted to branched materials having higher octane ratings. Additionally, alicyclic hydrocarbons (naphthenes) having at least about 6 carbon atoms, typically from about 6 to 50 carbon atoms, preferably 6 to 15 carbon atoms, can be converted to isomers thereof by contacting the same with hydrogen in the presence of the catalyst system described previously. Mixtures of acyclic and alicyclic hydrocarbons can be used as the process feedstock. In a typical commercial operation, a paraffin stream containing mixtures of various types of open chain and closed chain paraffins is used as the process feedstock. Typical isomerization reaction conditions are summarized below.

| Range | Low | High | Preferred |
|---|---|---|---|
| Temperature, °C | 0 | 150 | 30–75 |
| Hydrogen Partial Pressure, atm. | 0.1 | 140 | 0.3–25 |
| Reaction Time, min. | 0.5 | 1500 | 1–500 |
| Moles H$_2$/mole Hydrocarbon | 0.01 | 2.5 | 0.1–1.0 |
| Space Velocity, V/Hr./V | 0.05 | 50 | 0.25–20 |

In the alkylation of hydrocarbons with olefins, suitable olefinic starting materials are ethylene, propylene, butylenes, trimethyl ethylene and other isomeric pentenes, and similar higher monoolefinic hydrocarbons of either a straight chain or branched chain structure. Olefins containing 2 to 12 carbon atoms per molecule are preferred while olefins containing 2 to 5 carbon atoms per molecule are particularly preferred. The reaction mixtures may also contain some amounts of diolefins. Although it is desirable from an economic viewpoint to use the normally gaseous olefins as reactants, normally liquid olefins may also be used. Thus,, polymers, copolymers, interpolymers, crosspolymers, etc., of the above-mentioned olefins, as for example, propylene dimer, the diisobutylene and triisobutylene polymers, the codimer of normal and isobutylenes and the like may be used. The use of mixtures of two or more of the abovedescribed olefins is also envisioned for this purpose.

Hydrocarbon feedstocks that are suitable for use in alkylation processes include paraffins, aromatic alkyl substituted aromatic hydrocarbons and mixtures thereof. The paraffins as herein defined include the aliphatic and cycloaliphatic hydrocarbons. The aliphatic hydrocarbons (straight and branched chain materials) contain at least 1, preferably 1 to 12 carbon atoms per molecule, and may be exemplified by methane, ethane, propane, butanes, methylbutanes, n-pentane, methylpentanes, methylhexanes, and the like. The cycloaliphatic hydrocarbons (naphthenes) contain at least 5, preferably 5 to 15 carbon atoms per molecule, more preferably 6 to 12 carbon atoms and may be exemplified by methylcyclopentane, dimethylcyclopentane, methylcyclohexane, ethylcyclohexane, n-pentylcyclohexane and the like. Useful aromatic and alkyl aromatic hydrocarbons contain at least 6, preferably 6 to 20 carbon atoms per molecule and are exemplified by benzene, ethyl benzene, n-butyl benzene and the like. Other aliphatic or alicyclic hydrocarbons commonly found in conventional petroleum hydrocarbon light naphtha streams and the like may be present. Typical alkylation reaction conditions are summarized below.

| Range | Low | High | Preferred |
|---|---|---|---|
| Temperature, °C | −100 | +150 | −10 − +80 |
| Hydrogen Partial Pressure, atm. | 0.1 | 100 | 0.3 − 25 |
| Reaction Time, min. | 0.05 sec. | 60+ | 0.1 sec. − 45 |
| Space Velocity based on olefin, V/Hr./V | 0.01 | 1.0 | 0.04 − 0.2 |

The hydrocarbon feedstock employed in the present invention may be the total feedstock to the hydrocarbon conversion process, or only a portion thereof. In the case of isomerization, it is preferable to employ the entire feedstock in the extraction step to maximize the recovery of active or potentially active catalyst species from that portion of the catalyst stream being treated while, at the same time, affording the maximum protection to catalyst activity by pretreating the total feedstock with the catalyst stream for the removal of catalyst contaminants. However, in the case of alkylation, it may be preferably to extract only with the paraffinic portion of the feedstock, as introduction of olefins into the extraction zone may result in undesirable reactions under conditions not conducive to optimum alkylate yield.

While not wishing to be bound by any particular theory, we believe that the above-mentioned hydrocarbon conversion catalyst is deactivated or neutralized by contaminants normally present in an unrefined hydrocarbon feedstock or by the formation of catalyst complexes in situ during the hydrocarbon conversion reaction. Illustrative of the type of contaminants which can cause reduced activity of the present hydrocarbon conversion catalyst are inorganic materials such as water which may enter the reaction zone of the hydrocarbon conversion process in the feedstock or as a result of an operational mishap, metals and metal compounds resulting from corrosion of the reaction zone internals or present in heavier feedstocks, and organic material such as stable unsaturated ions generated during reaction, nitrogen-containing compounds, sulfur and oxygen-containing compounds, and the like. Although the present catalyst can tolerate amounts of contaminants that would typically destroy the activity of classic Friedel-Crafts catalyst systems, it is desirable that said feedstock, diluents and individual catalyst constituents be purified prior to use in the hydrocarbon conversion process to remove substantially all of the aforementioned contaminants in order to obtain maximum catalyst activity and catalyst life. By substantially is meant that at least 70 wt. %, preferably at least 80 wt. %, more preferably at least 90 wt. %, most preferably at least 95 wt. % of the water, sulfur impurities, metals and/or nitrogen-containing compounds will be removed from the hydrocarbon feedstock prior to or during the pretreat extraction process. The aforementioned contaminants may be removed from the hydrocarbon feedstock prior to extraction by any several commercially available processes, e.g. hydrotreating, clay treating, caustic treating, drying and the like.

It is preferred that the partially deactivated catalyst be contacted with the hydrocarbon feedstock in the presence of hydrogen. The amount of hydrogen present in the extraction zone during the extraction process is not critical provided at least a portion of the hydrogen is solubilized in the acid. The hydrogen serves to prevent undesirable side reactions by allowing the acid catalyst to saturate or hydrogenate unsaturated materials or precursors in or formed in the acid layer. The hydrogen, if present, may be present in the form of a hydrogen-containing gas which may be obtained from any number of sources including commercially available pure hydrogen, naphtha reformers, hydrogen plants, as well as the off-gases from any hydrotreating process or hydrogen donor organic molecules such as tetralin, methylcyclohexane, decalin, isobutane and the like. The term hydrotreating process is meant to include hydrofining, hydrocracking, hydrodesulfurization and the like or synthetic schemes in which hydrogen is a product. The hydrogen-containing gas may be pure or contain other gaseous materials such as nitrogen, light hydrocarbons ($C_1$-$C_{10}$) or carbon monoxide and the like. The hydrogen-containing gas may be introduced into the extraction zone alone or be mixed with the hydrocarbon feed prior to introduction into said zone. Preferably the hydrogen-containing gas will be dry.

Depending upon the temperature of the extraction zone and the particular hydrocarbon feedstock, the presence of hydrogen may not be required if the extraction is sufficiently rapid. For example, if the feedstock contains aromatic compounds and the extraction reaction is conducted at a temperature of about 40° C., hydrogen need not be present if the extraction can be completed within about 30 minutes. At 50° C., the extraction reaction should be completed within about 10 minutes. In the substantial absence of aromatic compounds, the extraction reaction can be conducted at temperatures less than 50° C. in the absence of hydrogen. However, it is preferable to have hydrogen present during said extraction to minimize degradation of the catalyst and thereby assure maximum recovery of active or potentially active catalyst.

It is essential that the extraction reaction be conducted at a temperature below the critical temperature of the Bronsted acid. Preferably, the temperature at which the extraction reaction is conducted will range from about 20° to about 75° C., more preferably from about 20° to about 60° C.

The pressure at which the extraction process is carried out is not critical to effecting the extraction and will depend upon the nature of the hydrocarbon feedstock being processed, the temperature during extraction as well as other variables. In general, the pressure should be sufficient to maintain at least a portion of one of the acid components and at least a portion of the hydrocarbon feedstock in the liquid phase. This may be expresssed in terms of hydrogen partial pressure which should be at least 0.1 atmospheres and may range from about 0.1 to about 100 atmospheres, preferably from about 0.1 to about 50 atmospheres, and most preferably from about 0.3 to about 30 atmospheres. The extraction process may be operated under a total pressure ranging from about 1 to about 150 atmospheres. Preferably, the extraction will be conducted substantially in the liquid phase.

The extraction occurs rather promptly and the contact time required need only be that sufficient to effect a substantial removal of contaminants from the hydrocarbon feedstock and the substantial recovery of the active or potentially active catalyst species from the partially deactivated hydrocarbon conversion catalyst. Thus, the contact time may vary from a second to several hours depending on the temperature, extraction efficiency and other interrelated variables. Generally, the contact time will vary from 1 second to about 5 hours, preferably from 1 second to about 2 hours, more preferably from 1 second to about 1 hour, and most preferably from about 1 second to about 30 minutes.

The hydrocarbon feedstock may be contacted with the partially deactivated catalyst in any suitable apparatus. Contacting may be effected in batch, multiple batch, semicontinuous, or continuous operation. For example, it may be carried out in continuous (differential) contacting equipment such as single or multiple mixer-settlers, simple gravity operated extractors without mechanical agitation, mechanically agitated extractors, centrifugal extractors, or packed or unpacked towers with or without mixing orifices. Preferably, a high efficiency multi-stage countercurrent extractor will be used. Equipment most suitable for a specific application can be selected by one skilled in the art from available equipment as described in, but not limited to, Sections 18 and 21 of the Fourth Edition of the "Chemical Engineers' Handbook" edited by John H. Perry (1963). Depending upon the catalyst system employed, the contacting equipment may not require the use of any special materials of construction, i.e. carbon steel may be quite satisfactory. However, alloy materials such as Alloy 20, Monel, aluminum 5052, aluminum 6061 and the like, as well as Teflon, may be used.

One of the product streams from the extraction zone is an extract phase which comprises substantially all, i.e. at least 80%, preferably at least 90% more preferably at least 95%, and most preferably at least 99%, of the hydrocarbon feedstock, said feedstock being substantially free of potential catalyst poisons, and a substantial portion, i.e. at least 25 wt. %, preferably at least 50 wt. %, more preferably at least 60 wt. %, and most preferably at least 70 wt. %, of the active or potentially active species present in the partially deactivated catalyst introduced into the extraction zone. Any catalyst contaminants not removed from the extraction zone in the raffinate phase will be removed in the extract phase. At least a portion but preferably all of the extract phase is then introduced into the hydrocarbon conversion process with or without further treatment.

The other product stream from the extraction zone is a raffinate phase which comprises a residue containing a major portion of deactivated catalyst (i.e. the contaminated or inactive Lewis acid component of the catalyst), some Bronsted acid component along with the contaminating catalyst poisons removed from both the hydrocarbon feedstock and the partially deactivated catalyst from the hydrocarbon conversion process, some dissolved hydrocarbon and perhaps some small amounts of hydrolyzed Lewis acid species. The raffinate phase may also cantain some solid material which comprises deactivated catalyst residues or sludge formed in the hydrocarbon conversion process that may be present in the partially deactivated catalyst stream entering the extraction zone or that may be formed by the reaction of contaminants in the hydrocarbon feedstock with the partially deactivated catalyst during extraction. At least 50%, preferably at least 75,%, and more preferably at least 90% of the deactivated catalyst present in the partially deactivated catalyst stream entering the extraction zone is removed therefrom via the raffinate phase. However, depending upon the amount of catalyst poisons introduced into the extraction zone with the hydrocarbon feedstock, the amount of deactivated catalyst species present in the raffinate phase may be more than the amount of deactivated catalyst species introduced into the extraction zone via the partially deactivated catalyst purge stream since active catalyst in the purge stream may be deactivated in the extraction zone by the catalyst poisons in the feedstock. The raffinate phase which comprises a major portion of the deactivated catalyst species present in the partially deactivated catalyst stream, as well as any deactivated species formed in the extraction zone as described above, may then be regenerated by a variety of means including incineration or chemical-metallurgical methods. Preferably, any volatile acid components (including the Bronsted acid) will be substantially removed from the raffinate phase prior to regeneration by means such as flashing, stripping with hydrogen or hydrocarbon vapor and the like. Some dissolved hydrogen will be present in both the extract and raffinate phase.

The volume ratio of partially deactivated catalyst to fresh hydrocarbon feedstock introduced into the extraction zone will range from about 1:20 to about 1:100,000 preferably from about 1:50 to about 1:10,000. In order to assure good contacting between the hydrocarbon and acid phases, it may be advantageous to recycle at least a portion of the raffinate phase through one or more stages so that the volume ratio will be increased so as to be in the range of from about 1:2 to about 1:20. In the case of a multistage extraction zone, at least a portion of the raffinate phase may be recycled to at least one stage comprising the zone, e.g. to the initial or an intermediate stage.

The process of this invention will be further described with reference to FIG. 1 which shows a preferred embodiment of the present invention. It is to be understood that the drawing is shown only in such detail as is necessary for a clear understanding of the invention and that no intention is made thereby to unduly limit the scope of this invention. Various items such as valves, compressors, instrumentation, as well as other process equipment and control means have been omitted therefrom for the sake of simplicity. Variations obvious to those having ordinary skill in the art of extraction processes are included within the board scope of the present invention.

Referring now to FIG. 1, a hydrocarbon conversion zone 1 and a countercurrent extraction zone 2 having a plurality of stages 3 are shown therein, with a partially deactivated catalyst stream and a hydrocarbon product stream leaving hydrocarbon conversion zone 1 via lines 4 and 5, respectively. As described above, both active or potentially active catalsyt species and deactivated catalyst species are present in the partially deactivated catalyst. In order to avoid an accumulation of catalyst contaminants and deactivated catalyst species within hydrocarbon conversion zone 1, a portion of partially deactivated catalyst stream 4 is introduced into extraction zone 2 via catalyst purge stream 6, the remaining portion of partially deactivated stream 4 being returned to hydrocarbon conversion zone 1 via line 7. A hydrocarbon feedstock 8, a hydrogen-containing gas 9 and hydrogen fluoride 10 are introduced into extraction zone 2 via line 11 and contacted with the catalyst purge stream 6. There results from said contacting an extract phase and a raffinate phase as defined above. The extract phase is sent to the hydrocarbon conversion zone 1 via line 12 while the raffinate phase is removed from extraction zone 2 via line 13. Active catalyst is added to the hydrocarbon conversion zone 1 via line 14 to replace the active or potentially active catalyst species not recovered from the catalyst purge stream 6 and the deactivated catalyst species leaving extraction zone 2 via line 13.

By using the method of the present invention, at least a portion of the active or potentially active species from a partially deactivated hydrocarbon conversion catalyst is recovered prior to regeneration while potential catalyst contaminants present in the feedstock to the hydrocarbon conversion process are substantially removed therefrom. Thus, this method considerably reduces the severity of or eliminates the need for other feed pretreatment, such as hydrofining for sulfur or nitrogen removal and feed drying. This method also has the advantage of reducing the size of the catalyst regeneration system since the active or potentially active catalyst species will have been removed therefrom and recycled to the hydrocarbon conversion process.

The following examples are presented to further illustrate the process of the present invention and are not intended to unduly restrict the limits of the claims appended hereto.

A set of experiments were conducted at room temperature and at different molar ratios of hydrogen fluoride to tantalum pentafluoride to simulate extraction of the hydrogen fluoride and the potentially active species, i.e. the tantalum pentafluoride, from a partially deactivated hydrocarbon conversion catalyst. An actual extraction was simulated by starting at a molar ratio of 10/1 and increasing said ratio at four different composition points to simulate the different stages of an actual extraction wherein more tantalum pentafluoride is being extracted. Four or five extractions were conducted at each molar ratio to obtain replicate results before the catalyst deactivated substantially due to poor hydrogen contacting. Such poor contacting could be easily avoided in a commercial sized unit. The results of the extractions provided data for the accompanying figure which shows the efficiency of the present invention in the recovering of potentially active catalyst species.

EXAMPLE 1

Into a one liter Parr Model 4521 Hastellow C stirred reactor in a dry box was placed tantalum pentafluoride (41.1 g, 0.15 mole). Hydrogen fluoride (29.95 g, 1.5 mole) was added from a pressurized cylinder through a gas sampling valve by direct connection. A hydrocarbon feedstock (500 cc, 335 g. 3.9 mole) containing n-hexane (90 mole %) and cyclohexane (10 mole %) was then introduced from a precharged cylinder pressurized with hydrogen. The stirrers (2) were turned on at 1000 rpm and the reactor temperature and pressure were adjusted to 23° C, and 230 psig (16.7 atmospheres), respectively. Extraction of the tantalum pentafluoride was then simulated by repetitive removal of the hydrocarbon saturated with catalyst and recharging fresh feed. The samples taken were analyzed by wet chemical methods for determination of tantalum to give the following results:

| Extraction No. | Hydrocarbon Solvent | | Tantalum Pentafluoride | | |
|---|---|---|---|---|---|
| | Wt. (g.) | Cumulative Wt. (g.) | wppm | Actual Wt.(g) | % Unrecovered |
| 1 | 329.71 | 329.71 | 6688 | 2.22 | 94.6 |
| 2 | 342.79 | 660.24 | 1427 | 0.49 | 93.5 |
| 3 | 334.70 | 1003.03 | 717 | 0.24 | 92.9 |
| 4 | 328.42 | 1337.73 | 943 | 0.31 | 92.1 |
| 5 | 330.53 | 1666.15 | 1420 | 0.47 | 91.0 |
| 6 | 333.24 | 1999.39 | 1498 | 0.50 | 89.8 |
| 7 | 339.53 | 2338.92 | 1089 | 0.37 | 88.9 |
| 8 | 329.81 | 2668.73 | 969 | 0.32 | 88.1 |
| 9 | 341.06 | 3009.79 | 1318 | 0.45 | 87.0 |

-continued

| Extraction No. | Hydrocarbon Solvent | | Tantalum Pentafluoride | | |
|---|---|---|---|---|---|
| | Wt. (g.) | Cumulative Wt. (g.) | wppm | Actual Wt.(g) | % Unrecovered |
| 10 | 335.41 | 3345.20 | 1518 | 0.51 | 85.8 |

Thus, at a hydrogen fluoride to tantalum pentafluoride molar rate of 10/1, about 0.41 grams of tantalum pentafluoride will dissolve in 335 g of hydrocarbon solvent. The high concentration of tantalum pentafluoride in Extraction 1 is due to the initial presence of some undissolved tantalum pentafluoride.

EXAMPLE 2

The same experiment shown in Example 1 was repeated using the same feedstock and reactor conditions of 24° C. and 16.7 atmospheres. However, tantalum pentafluoride (15.0 g, 0.054 mole) and hydrogen fluoride (20.10 g, 1.0 mole) were added such that the molar ratio of hydrogen fluoride to tantalum pentafluoride was 18.5/1. The molar ratio of hydrocarbon feedstock to hydrogen fluoride was about 4/1. Extractions simulating the recovery of tantalum pentafluoride were conducted as in Example 1. The results from this experiment are shown below.

| Extraction No. | Hydrocarbon Solvent | | Tantalum Pentafluoride | | |
|---|---|---|---|---|---|
| | Wt. (g.) | Cumulative Wt. (g.) | wppm | Actual Wt.(g) | % Unrecovered |
| 1 | 316.71 | 316.71 | 915 | 0.29 | 98.1 |
| 2 | 339.39 | 656.10 | 942 | 0.32 | 95.9 |
| 3 | 330.71 | 986.81 | 1027 | 0.34 | 93.7 |
| 4 | 338.09 | 1324.90 | 1467 | 0.50 | 90.3 |
| 5 | 331.19 | 1656.09 | 754 | 0.25 | 88.7 |
| 6 | 329.90 | 1985.99 | 485 | 0.16 | 87.6 |
| 7 | 323.87 | 2309.86 | 586 | 0.19 | 86.3 |
| 8 | 331.49 | 2641.35 | 392 | 0.13 | 85.5 |
| 9 | 338.07 | 2979.42 | 384 | 0.13 | 84.6 |
| 10 | 343.50 | 3322.92 | 204 | 0.07 | 84.1 |

Thus, at a hydrogen fluoride to tantalum pentafluoride molar ratio of 18.5/1, about 0.33 grams of tantalum pentafluoride will dissolve in 335 g of hydrocarbon solvent. Extractions 6–10 show the effects of poor hydrogen contacting as well as the continuous depletion of the hydrogen fluoride content of the catalyst phase and were not included in the averaging.

EXAMPLE 3

The experiments of Examples 1 and 2 were repeated using the same feedstock and reactor conditions of 24° C. and 16.7 atmospheres. However, tantalum pentafluoride (8.0 g, 0.029 mole) and hydrogen fluoride (20.32 g., 1.02 mole) were added such that the molar ratio of hydrogen fluoride to tantalum pentafluoride was 35/1. The results from this experiment were analyzed as before and are shown below:

| Extraction No. | Hydrocarbon Solvent | | Tantalum Pentafluoride | | |
|---|---|---|---|---|---|
| | Wt. (g.) | Cumulative Wt. (g.) | wppm | Actual Wt.(g) | % Unrecovered |
| 1 | 318.70 | 318.70 | 1160 | 0.37 | 95.4 |
| 2 | 327.59 | 646.29 | 580 | 0.19 | 93.0 |
| 3 | 335.99 | 982.28 | 446 | 0.15 | 91.1 |
| 4 | 338.08 | 1320.36 | 443 | 0.14 | 89.4 |
| 5 | 338.82 | 1659.18 | 472 | 0.16 | 87.4 |
| 6 | 331.05 | 1990.23 | 272 | 0.09 | 86.3 |
| 7 | 341.94 | 2332.17 | 263 | 0.09 | 85.1 |
| 8 | 326.60 | 2658.77 | 337 | 0.11 | 83.8 |
| 9 | 336.56 | 2995.33 | 184 | 0.06 | 83.0 |

-continued

| Extraction No. | Hydrocarbon Solvent | | Tantalum Pentafluoride | | |
|---|---|---|---|---|---|
| | Wt. (g.) | Cumulative Wt. (g.) | wppm | Actual Wt.(g) | % Unrecovered |
| 10 | 332.59 | 3327.92 | 361 | 0.12 | 81.5 |

Thus, at a hydrogen fluoride to tantalum pentafluoride molar ratio of 35/1, about 0.16 grams of tantalum pentafluoride dissolves in 335 g of the solvent. As in Example 2, extractions 6–10 show the effects of poor hydrogen contacting and were not included in the averaging.

EXAMPLE 4

The experiment of Examples 1, 2 and 3 were repeated using the same feedstock and reactor conditions of 26° C. and 16.7 atmospheres. However, tantalum pentafluoride (2.77 g, 0.01 mole) and hydrogen fluoride (20.5 g, 1.03 mole) were added such that the molar ratio of hydrogen fluoride to tantalum pentafluoride was 100/1. The results from this experiment were analyzed as before and are shown below:

| Extraction No. | Hydrocarbon Solvent | | Tantalum Pentafluoride | | |
|---|---|---|---|---|---|
| | Wt. (g.) | Cumulative Wt. (g.) | wppm | Actual Wt.(g) | % Unrecovered |
| 1 | 321.79 | 321.79 | 0 | 0 | |
| 2 | 332.90 | 654.69 | 90 | 0.03 | |
| 3 | 336.53 | 991.22 | 59 | 0.02 | |
| 4 | 328.91 | 1320.13 | 0 | 0 | |
| 5 | 336.69 | 1656.82 | 0 | 0 | |
| 6 | 338.96 | 1995.78 | 59 | 0.02 | |

These results indicate that less tantalum pentafluoride will be extracted from the partially deactivated catalyst as the molar ratio of hydrogen fluoride to tantalum pentafluoride approach 100/1; i.e., as the catalyst becomes more diluted less potentially active species will be removed.

The results from these experiments are shown in FIG. 2 and indicate that about 70 wt. % of the tantalum pentafluoride, i.e. the potentially active catalyst species, can be successfully extracted from the present partially deactivated hydrocarbon conversion catalyst.

It should be noted that the solubility of hydrogen fluoride in hydrocarbon is greater than that of tantalum pentafluoride. Thus, since the ratio of hydrocarbon solvent to partially deactivated catalyst is quite high, the extraction zone could become depleted in hydrogen fluoride, which serves to dissolve the tantalum pentafluoride. Thus, it may be desirable to add additional hydrogen fluoride to the extraction zone, e.g. to the hydrocarbon feedstock entering said zone, to avoid extracting the partially deactivated catalyst to dryness therein, i.e., to a point such that a portion of the tantalum pentafluoride will solidify with the extraction zone. This similarly applies to other Lewis and Bronsted acids.

It should also be noted that some conversion of the hydrocarbon feedstock may occur in the extraction zone in advance of the hydrocarbon conversion process since at least a portion of said feedstock will be contacted with at least a portion of the active catalyst present in the partially deactivated catalyst. Thus it may be desirable to introduce at least a portion of the extract phase into the hydrocarbon conversion process.

What is claimed is:

1. In a hydrocarbon conversion process which comprises contacting a hydrocarbon feedstock with a liquid phase catalyst comprising tantalum pentafluoride, niobium pentafluoride or mixtures thereof in combination with at least an equimolar amount of hydrogen fluoride, thereby forming a partially deactivated catalyst which contains active or potentially active catalyst species and deactivated catalyst species, the improvement which comprises maintaining hydrocarbon conversion activity of the catalyst in said process by the steps comprising 1. passing a purge stream of said partially deactivated catalyst into an extraction zone, the remaining partially deactivated catalyst being returned to said hydrocarbon conversion process;
2. contacting, in said extraction zone, the purge stream of step (1) with said hydrocarbon feedstock prior to introducing said feedstock into said hydrocarbon conversion process, the amount of said feedstock being sufficient to remove at least 25 wt. % of the active or potentially active catalyst species from said purge stream, said contacting occurring substantially in the liquid phase and at a temperature below the critical temperature of the hydrogen fluoride, the volume ratio of said purge stream to said hydrocarbon feedstock ranging from about 1:20 to about 1:100,000;
3. forming an extract phase containing substantially all of the hydrocarbon feedstock employed in step (2) and substantially all of the active or potentially active catalyst species removed in step (2) and a raffinate phase containing at least 50 wt. % of the deactivated catalyst species present in the purge stream of step (1);
4. passing at least a portion of said extract phase from said extraction zone to said hydrocarbon conversion process;
5. withdrawing a raffinate phase containing said deactivated catalyst species from said extraction zone; and
6. adding active catalyst to said hydrocarbon conversion process in an amount sufficient to replace the active or potentially active catalyst species not returned to the hydrocarbon conversion process in step (4) and the deactivated catalyst species withdrawn in step (5).

2. The process of claim 1 wherein hydrogen is present in the extraction zone in an amount sufficient to maintain a hydrogen partial pressure of at least 0.1 atmospheres.

3. The process of claim 1, wherein the hydrocarbon feedstock comprises (1) a component selected from the group consisting of an aliphatic hydrocarbon having at least one carbon atom, a cycloaliphatic hydrocarbon having at least 5 carbon atoms, an aromatic and alkyl aromatic hydrocarbon having at least 6 carbon atoms and mixtures thereof and (2) olefins containing from 2 to 12 carbon atoms per molecule.

4. In a hydrocarbon conversion process which comprises contacting a hydrocarbon feedstock with a liquid phase catalyst comprising tantalum pentafluoride, niobium pentafluoride or mixtures thereof in combination with hydrogen fluoride, the molar ratio of the hydrogen fluoride to the pentafluoride component of the catalyst being at least 2:1, thereby forming a partially deactivated catalyst which contains active or potentially active catalyst species and deactivated catalyst species, the improvement which comprises maintaining hydrocarbon conversion activity of the catalyst in said process by the steps comprising 1. passing a purge stream of said partially deactivated catalyst into an extraction zone, the remaining partially deactivated catalyst being returned to said hydrocarbon conversion process;
2. contacting, in said extraction zone, the purge stream of step (1) with said hydrocarbon feedstock prior to introducing said feedstock into said hydrocarbon conversion process, the amount of said feedstock being sufficient to remove at least 25 wt. % of the active or potentially active catalyst species from said purge stream, said contacting occurring substantially in the liquid phase and at a temperature below the critical temperature of the hydrogen fluoride, the volume ratio of said purge stream to said hydrocarbon feedstock ranging from about 1:20 to about 1:100,000;
3. forming an extract phase containing substantially all of the hydrocarbon feedstock employed in step (2) and substantially all of the active or potentially active catalyst species removed in step (2) and a raffinate phase containing at least 50 wt. % of the deactivated catalyst species present in the purge stream of step (1);
4. passing at least a portion of said extract phase from said extraction zone to said hydrocarbon conversion process;
5. withdrawing a raffinate phase containing said deactivated catalyst species from said extraction zone; and
6. adding active catalyst to said hydrocarbon conversion process in an amount sufficient to replace the active or potentially active catalyst species not returned to the hydrocarbon conversion process in step (4) and the deactivated catalyst species withdrawn in step (5).

5. The process of claim 4 wherein at least 50 wt. % of the active or potentially active catalyst species is removed in step (2).

6. The process of claim 4 wherein hydrogen is present in said extraction zone in an amount sufficient to maintain a hydrogen partial pressure within the range of from about 0.1 to about 100 atmospheres.

7. The process of claim 4 wherein extraneous hydrogen fluoride is added to the extraction zone.

8. The process of claim 4 wherein the hydrocarbon feedstock comprises (1) a component selected from the group consisting of $C_1$–$C_{12}$ aliphatic hydrocarbons, $C_5$–$C_{15}$ cycloaliphatic hydrocarbons, $C_6$–$C_{20}$ aromatic and alkyl aromatic hydrocarbons and mixtures thereof and (2) olefins containing from 2 to 12 carbon atoms per molecule.

9. The process of claim 4 wherein the extraction zone is multistage and at least a portion of the raffinate phase is recycled to at least one stage of said multistage extraction zone.

10. The process of claim 4 wherein the temperature in the extraction zone ranges from about 20° to about 75° C.

11. The process of claim 4 wherein potential catalyst poisons present in said hydrocarbon feedstock are substantially removed therefrom prior to said extraction zone.

12. In an isomerization process which comprises contacting a hydrocarbon feedstock comprising a saturated acyclic hydrocarbon having at least four carbon atoms, a saturated alicyclic hydrocarbon having at least six carbon atoms or mixtures thereof, with a liquid phase catalyst comprising tantalum pentafluoride, niobium pentafluoride or mixtures thereof in combination with at least an equimolar amount of hydrogen fluoride, thereby forming a partially deactivated catalyst which contains active or potentially active catalyst species and deactivated catalyst species, the improvement which comprises maintaining hydrocarbon conversion activity of the catalyst in said process by the steps comprising 1. passing a purge stream of said partially deactivated catalyst into an extraction zone, the remaining partially deactivated catalyst being returned to said isomerization process;
2. contacting, in said extraction zone, the purge stream of step (1) with said hydrocarbon feedstock prior to introducing said feedstock into said isomerization process, the amount of said feedstock being sufficient to remove at least 25 wt. % of the active or potentially active catalyst species from said purge stream, said contacting occurring substantially in the liquid phase, at a temperature below the critical temperature of the hydrogen fluoride and at a hydrogen partial pressure of at least 0.1 atmospheres, the volume ratio of said purge stream to said hydrocarbon feedstock ranging from about 1:20 to about 1:100,000;
3. forming an extract phase containing substantially all of the hydrocarbon feedstock employed in step (2) and substantially all of the active or potentially active catalyst species removed in step (2) and a raffinate phase containing at least 50 wt. % of the deactivated catalyst species present in the purge stream of step (1);
4. passing at least a portion of said extract phase from said extraction zone to said isomerization process;
5. withdrawing a raffinate phase containing said deactivated catalyst species from said extraction zone; and
6. adding active catalyst to said isomerization process in an amount sufficient to replace the active or potentially active catalyst species not returned to the isomerization process in step (4) and the deactivated catalyst species withdrawn in step (5).

13. The process of claim 12 wherein the molar ratio of tantalum pentafluoride, niobium pentafluoride or mixtures thereof to hydrogen fluoride is at least 5:1.

* * * * *